(12) United States Patent  
Willemstyn

(10) Patent No.: US 6,893,428 B2  
(45) Date of Patent: May 17, 2005

(54) OVER-WRAP BAG ENCLOSURE FOR STERILE CONNECTORS

(76) Inventor: Benjamin R. Willemstyn, 17 Little Silver Pkwy., Little Silver, NJ (US) 07739

( * ) Notice: Subject to any disclaimer, the term of this patent is extended or adjusted under 35 U.S.C. 154(b) by 0 days.

(21) Appl. No.: 09/996,977

(22) Filed: Nov. 20, 2001

(65) Prior Publication Data

US 2002/0065505 A1 May 30, 2002

Related U.S. Application Data

(60) Provisional application No. 60/253,266, filed on Nov. 27, 2000.

(51) Int. Cl.$^7$ ................................................ A61M 5/32
(52) U.S. Cl. .................... 604/533; 604/263; 604/163
(58) Field of Search ............................. 604/408, 905, 604/326, 533, 263, 163, 339; 422/61, 99; 206/370, 363–66, 69; 220/62.22; 383/210.1; 128/912; 138/96; 285/45, 53

(56) References Cited

U.S. PATENT DOCUMENTS

| | | | | |
|---|---|---|---|---|
| 2,838,046 A | * | 6/1958 | Butler ........................ | 604/408 |
| 3,006,341 A | * | 10/1961 | Poitras ....................... | 604/251 |
| 4,253,500 A | * | 3/1981 | Williams ..................... | 141/1 |
| 4,523,679 A | * | 6/1985 | Paikoff et al. .............. | 206/370 |
| 4,657,540 A | * | 4/1987 | Iwamoto et al. ........... | 604/408 |
| 4,925,448 A | * | 5/1990 | Bazaral ..................... | 604/171 |
| 5,054,821 A | * | 10/1991 | Hillstead .................... | 285/321 |
| 5,088,994 A | * | 2/1992 | Porat et al. ................ | 604/408 |
| 5,391,163 A | * | 2/1995 | Christine et al. .......... | 604/408 |
| 5,843,049 A | * | 12/1998 | Heilmann et al. ......... | 604/275 |
| 5,915,407 A | * | 6/1999 | West .......................... | 137/223 |
| 5,932,132 A | * | 8/1999 | Plemons ..................... | 219/769 |
| 6,039,718 A | * | 3/2000 | Niedospial, Jr. ........... | 604/408 |
| 6,080,138 A | * | 6/2000 | Lemke et al. .............. | 604/263 |
| 6,183,460 B1 | * | 2/2001 | Smith et al. ............... | 604/408 |
| 6,200,300 B1 | * | 3/2001 | Petriekis et al. ........... | 604/408 |

* cited by examiner

Primary Examiner—Angela D. Sykes  
Assistant Examiner—Leslie Deak  
(74) Attorney, Agent, or Firm—Robert M. Skolnik

(57) ABSTRACT

A hose barb connector or sanitary adapter connector can be attached to various types of containers intended for use in sterile operations, such as in a biotechnology and pharmaceutical fluid processing container system. An over-wrap bag such as a poly-bag (ZIP-LOC® or other type) attached by heat welding to a flange formed near the middle of the connector. The over-wrap bag maintains the sterility of the enclosed end of the connector. The other end of the connector is typically attached to a piece of tubing or conduit in communication with another larger bag, which has been rendered sterile collectively with the connector. Sterile fluids pumped into the bag, either though the connector itself, or through some other opening in the larger bag, will not be contaminated. In another embodiment, where the connector is not attached to another sterile fluid containing bag and it is desired to maintain the entire connector sterile, both ends of the connector (including the attached over-wrap bag) are enclosed by another poly-bag.

12 Claims, 5 Drawing Sheets

OVER-WRAP BAG ENCLOSURE FOR STERILE CONNECTORS

CROSS-REFERENCE TO RELATED APPLICATIONS

This application discloses and claims the invention described in U.S. Provisional Application 60/253,266, filed Nov. 27, 2000.

BACKGROUND OF THE INVENTION

1. Field of the Invention

The present invention relates to a sterile connector, which may be used in biotechnology and pharmaceutical fluid processing or other applications where sterility of both ends of a fluid connector is required.

2. Description of the Related Art

Various devices that attach to plastic bag to a connector are shown in the prior art.

Child, 4,301,796 shows a connector or seal unit 41 to which plastic bag 36 is attached. Also, an end 42 of a bag is heat sealed over a bulb 43.

Field, 4,636,412 shows a flange 13 on a connector to which plastic bag 2 is welded.

LaFleur, 4,817,824, FIG. 16, heat seals bag 198 to flange 200 of a spout, 190.

Hammond, et al., 4,830,205, seals a curved base 22 of a baby bottle nipple to portions of a plastic container.

Stumpf, 4,887,912 discloses a bag welded to flange 8 of pipe socket 7.

Stricklin, et al, 5,609,195, FIG. 5, for example, shows a spout 38 having a flange 128 formed thereon to which plastic page 132 is welded.

Ropiak, et al., 5,896,989, shows a plastic outer bag sealed to a plastic inner bag.

Loeffler, 6,006,917 teaches a packaging system for maintaining sterility by vacuum fitting an outer bag to an inner bag.

Walters, et al, 6,048,640, disclose packaging medical electrodes.

SUMMARY OF THE INVENTION

The present invention is a hose barb connector or sanitary adapter connector, which can be attached to various types of fluid processing systems intended for use in sterile, or non-sterile, fluid processing operations. Such equipment and operations are common in the biotechnology, diagnostic and pharmaceutical manufacturing industries where fluid processing systems are critical to successful purification of products. The invention employs an over-wrap bag such as a poly-bag (ZIP-LOC® or other type) attached by heat welding to a flange formed near the middle of the connector. The over-wrap bag maintains the sterility of the enclosed end of the connector. The other end of the connector is typically attached to a piece of tubing or conduit in communication with another larger bag, which has been rendered sterile collectively with the connector. Sterile fluids pumped into or out of the bag, either though the connector itself, or through some other opening in the larger bag, will not be contaminated. In another embodiment of the invention, the connector and welded bag is placed inside a larger pouch and rendered sterile collectively. In use, a user can remove the large outer pouch under a sterile field, connect tubing to the exposed, yet still sterile, portion of the connector and then transport the tubing and connector outside of the sterile field whilst maintaining the sterility of the portion of the connector still sealed within the inner poly-bag.

The connecting flange formed to support the attachment of the first poly-bag may be formed in a variety of shapes, curved, or formed flat. The over-wrap bag and connector may be constructed from a variety of materials such as polyethylene, TYVEK®, polypropylene, Teflon®, Silicone, C-Flex®, ethylene vinyl acetate, PVC, polycarbonate, PVDF, etc. These materials are typically laminated or coextruded to provide an overwrap bag that has desirable properties to protect the connector (tear and puncture resistance, as well as gas barrier properties) while still being capable of sealing to the connector itself.

Sterility is required in biotechnology and pharmaceutical fluid processing applications. Typically, fluid processing in the biotechnology and pharmaceutical manufacturing industry involves the use of sterile fluids stored in large plastic bags. The fluids contain the active ingredients, or other process solutions such as buffers or preparatory agents, being manufactured by the pharmaceutical or biotechnology company. These fluids are moved into and out of the sterile bags by connecting tubing or conduits from the process equipment to ports on the bags previously fitted with tubing and connectors that were attached when the bag was manufactured. After connecting to the bag, fluid can be pumped into or out the bag for use in further operations.

The connector(s) of the invention will be attached to a large fluid-processing bag via a piece of tubing. The large bag, equipped with a connector(s) is then packaged, in its entirety, within one or two large poly-seal pouch and subsequently sterilized via, for example, gamma-irradiation sterilization or by exposure to steam in an autoclave (two outer poly-pouches are often used for use in pharmaceutical clean-room applications). In use, a biotechnology or pharmaceutical fluid processing technician will use the connector(s) on the bag to fill the bag with a process solution. This is achieved by removing the polybag overwrap that protects the end connection of the invention (in this case on the inlet of the bag) under a sterile field and connecting it to the equipment that will feed sterile solution into the bag. When the bag is filled, the tubing is clamped off or heat-sealed closed. A second connection on the bag serves as an outlet. The polybag overwrap maintains the sterility of the outlet end-connection until the processing technician needs to access it. In which case, the polybag overwrap is removed under a sterile field for connection to the next piece of tubing and/or equipment in the process. In situations where absolute sterility of the end-connection is not required, the overwrap system can be used outside of a sterile field with the knowledge that the overwrap system will keep the end-connection sterile until the moment the polybag is removed, this minimizing unnecessary additional bioburden. Often times, the large bags are highly customized depending on the manufacturers process. It is not uncommon for there to be more than one inlet or outlet that would derive benefit from the utility of the invention.

A second embodiment of the invention employs an additional plastic outer bag enclosing the entire connector and bag assembly. The part and outer pouch is then collectively sterilized via, for example, gamma irradiation or through exposure to steam in an autoclave. In use, the outer bag is opened in a sterile field and the exposed end of the connector is attached to sterile tubing. The second end of the connector remains sealed in its bag (heat sealed to a flange formed on the connector) and maintains the sterility of the enclosed end of the connector when removed from the sterile field for transport. The heat-sealed bag is removed, when required, in a sterile field for connection to other equipment, or simply kept intact during transport in order to maintain a lower level of bioburden in the tubing system until connection to equipment is required.

A principal object and advantage of the invention is the provision of a sterile enclosure for one end of a fluid connector.

Another object and advantage of the invention is the provision of a further sterile enclosure for both ends of a fluid connector.

A still further object of the invention is the provision of a sterile connector where the enclosure for one end of the connector is heat sealed to a flange on the connector.

Another object and advantage of the invention is the provision of sterile connector which can be used in two steps; a first step connecting a first sterile end of the connector to a source of sterile fluids while maintaining the sterility of the second end of the connector so that it can be transported in non-sterile areas.

The foregoing, as well as further objects and advantages of the invention will become apparent to those skilled in the art from a review of the following detailed description of my invention, reference being made to the accompanying drawings.

DETAILED DESCRIPTION OF THE PREFERRED EMBODIMENTS

Figure 1:
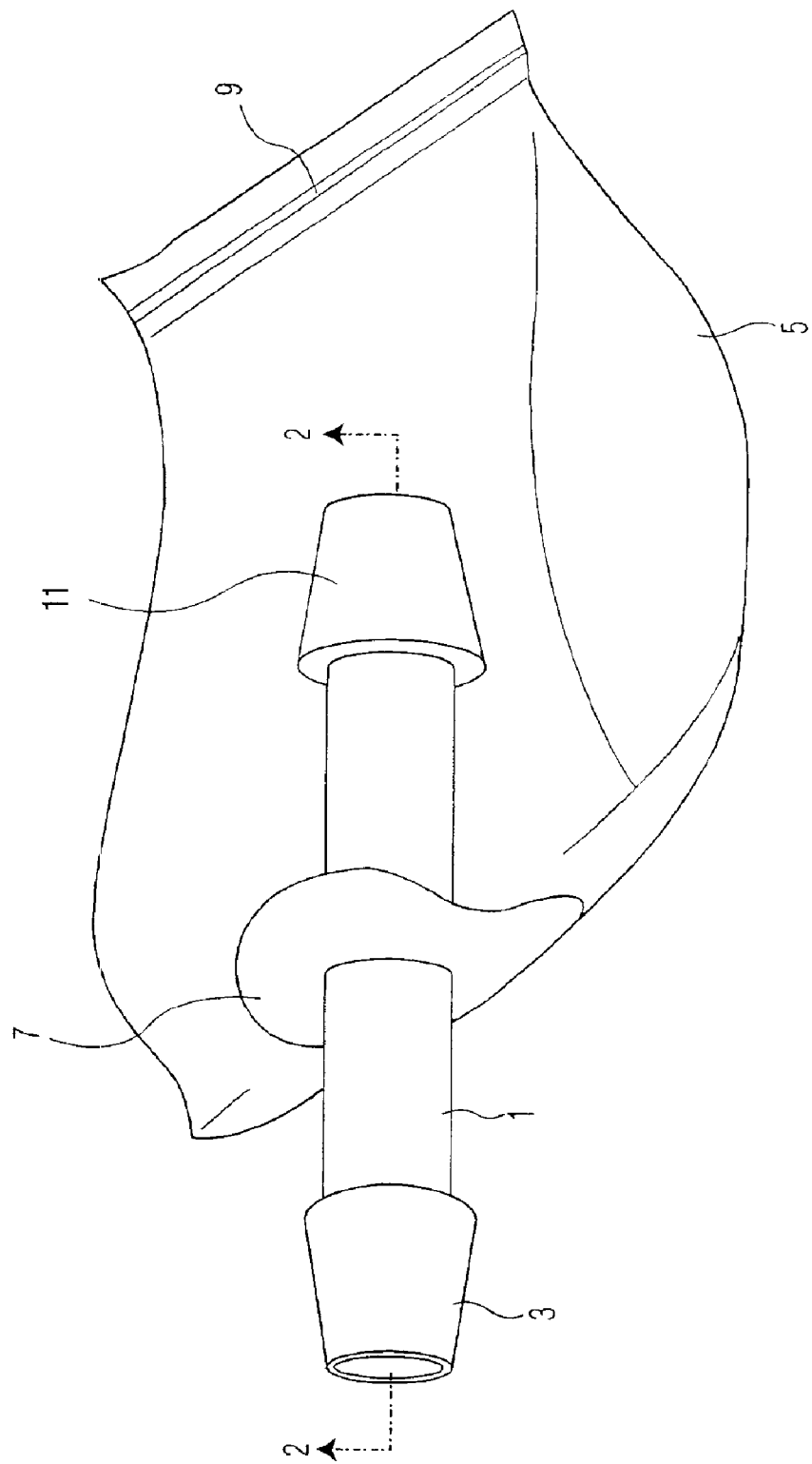
FIG. 1 is a perspective view of my invention.
Figure 2:
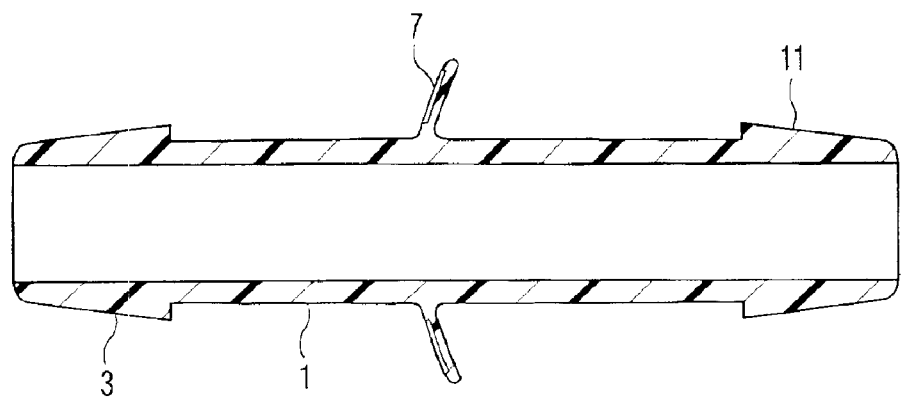
FIG. 2 is a side view of one embodiment of my invention.

Like reference numerals have been used to designate like parts of the invention in FIGS. 1–4. As shown in FIGS. 1–2, a fluid connector has a hollow barrel 1 and connector ends 3 and 11 formed at opposite ends of barrel 1. A flange 7 is attached to and may be formed integrally with barrel 1 at a location on barrel 1 which is intermediate the ends 3 and 11. In FIG. 1, a poly-bag 5 having a ZIP-LOC® closure 9, for example is affixed to the flange 7 by heat sealing. This embodiment displays typical hose barb connections on each side.

Figure 3:
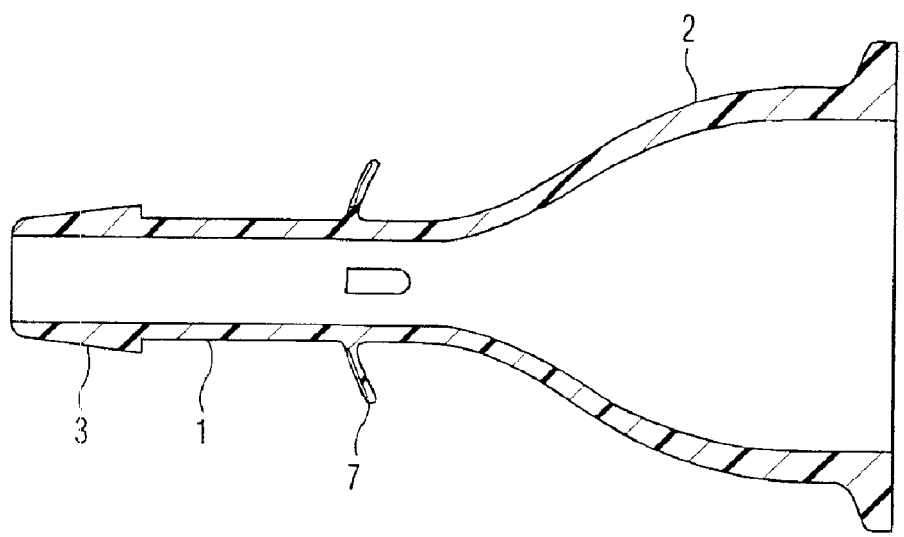
FIG. 3 is a side view of another embodiment of my invention.

FIG. 3 is a side view of another embodiment of my invention. The embodiment of FIG. 3 is similar to the embodiment of FIG. 2; however, one of the connection ends is formed to connect to a sanitary style flanged connector. In FIG. 3, the barrel 1 has connecting end 3 and flange 7 as in FIG. 2. A connector end 2 having a large diameter is formed on an end of barrel 1 opposite the connector 3.

Figure 4:
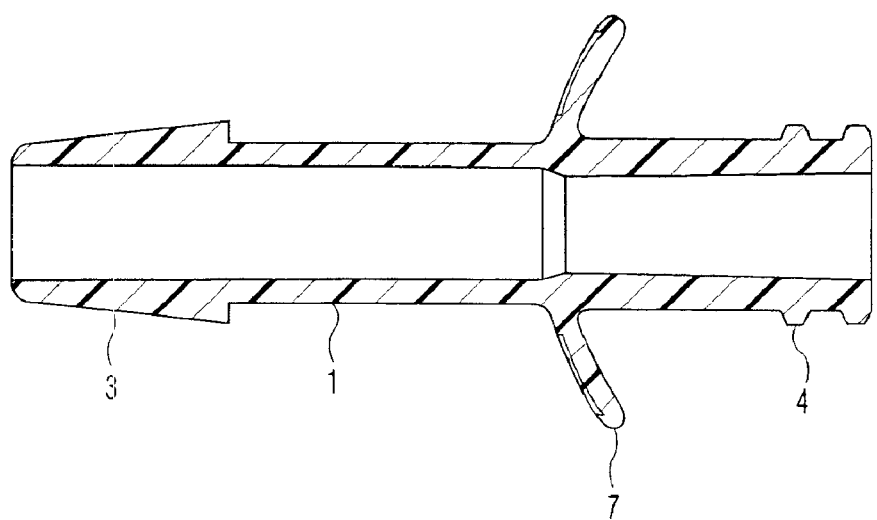
FIG. 4 is a side view of another embodiment of my invention.

FIG. 4 is a side view of another embodiment of my invention. The embodiment of FIG. 4, substitutes LUER® fitting 4 for connector end 11. The LUER® fitting is widely used in the medical and biological fields.

Figure 5:
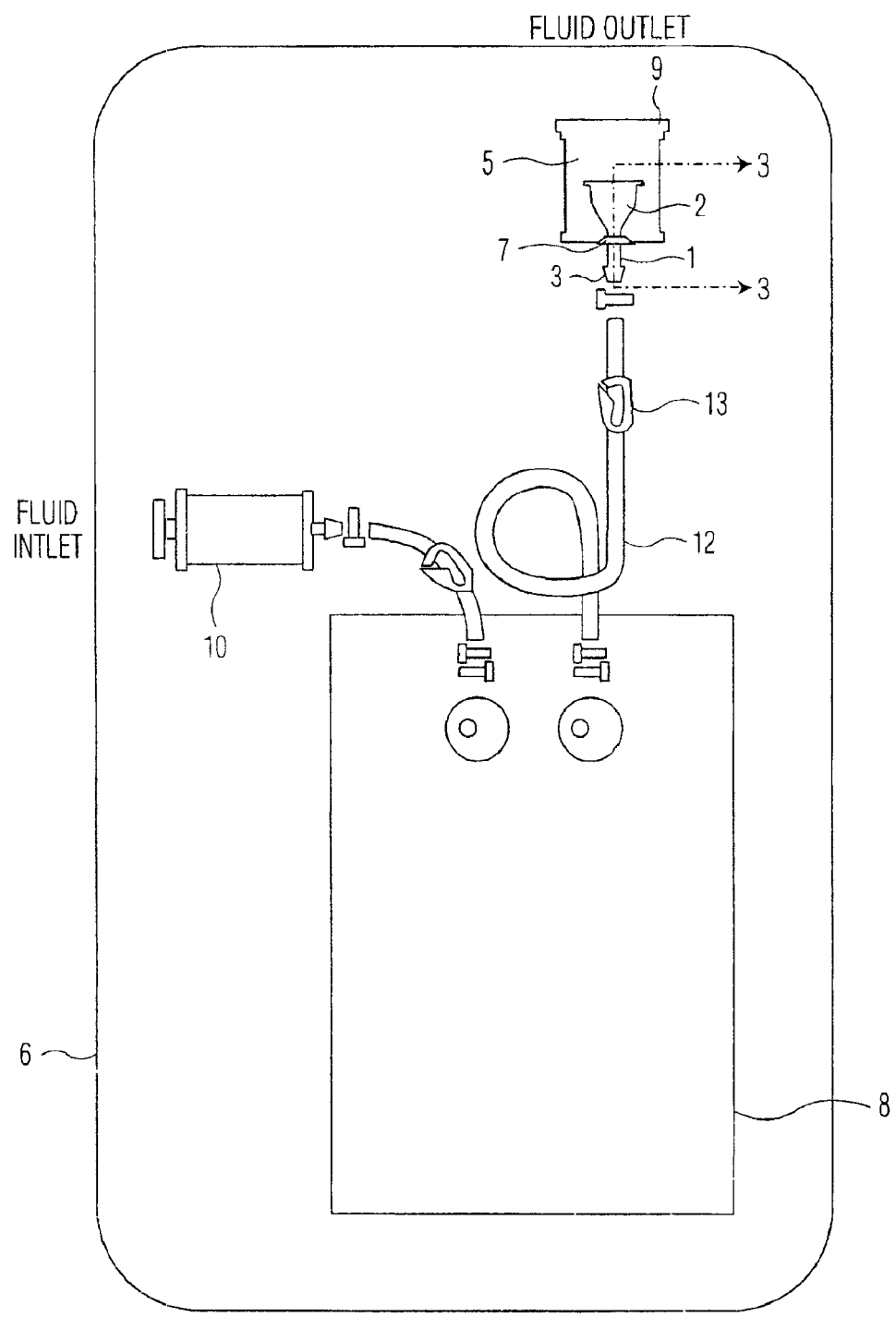
FIG. 5 is a diagrammatic view of my invention as used in biotechnology and pharmaceutical fluid processing.

FIG. 5 is a diagrammatic view of my invention as used in biotechnology and pharmaceutical fluid processing. A fluid container 8 is housed in a protective poly bag 6. Fluid container 8 has a fluid inlet shown generally at 10 and a fluid outlet including tubing 12, clamp 13, and cable tie 14. The embodiment of FIGS. 3 is attached to the end of tubing 12. More particularly, the connector having barrel 1, flange 7 enlarged connector 2 is enclosed in protective bag 5 which may include ZIP-LOC® 9. The bag 5 is heat welded to flange 7.

It has been found that an additional heat weld to an approximate ¾" length of film extending beyond the closure of the zipper enhances the sterile barrier provided at the zipper, protects the zipper from undesired opening, and provided a visual indicia of possible tampering. If this additional weld is employed, the operator must first cut away the heat weld with a scissor or knife and then pop open the zipper. The zipper cannot be opened unless the heat weld is cut away.

Further modifications to the apparatus of the invention may be made without departing from the spirit and scope of the invention.

I claim:

1. A connector assembly for containers used in sterile operations comprising: a connector having two ends and a flange formed thereon at a location which is intermediate said two ends; and an over-wrap bag enclosing one of said ends, said over-wrap bag being attached to said flange for maintaining sterility of said enclosed end; the connector assembly further comprising a second bag for enclosing said connector and said over-wrap bag for maintaining the sterility of said both ends of said connector assembly.

2. The connector assembly of claim 1 wherein said flange is curved.

3. The connector assembly of claim 1 wherein said flange is flat.

4. The connector assembly of claim 1 wherein the end of said connector which is not enclosed is attached to a large fluid-processing bag.

5. The connector assembly of claim 4, further including another bag enclosing said large fluid-processing bag, said connector and said over-wrap bag.

6. A sterile connector assembly comprising: a connector having two ends; a flange formed on said connector intermediate said two ends; a sealing bag attached to said flange enclosing one end of said connector; and a second bag enclosing the said connector and said sealing bag for double sealing said end of said connector enclosed by said sealing bag, whereby said second bag is open in a sterile field so that the exposed end of the connector may be attached to sterile tubing said other end of said connector remaining sealed in said sealing bag to maintain its sterility.

7. The sterile connector assembly of claim 1 wherein said over-wrap bag is a zipper-locking bag.

8. The sterile connector assembly of claim 7 wherein said over-wrap bag is heat sealed adjacent said zipper lock to prevent said zipper lock from opening unless said heat seal is cut away.

9. The sterile connector assembly of claim 6 wherein said flange is curved.

10. The sterile connector assembly of claim 6 wherein said flange is flat.

11. The sterile connector assembly of claim 6 wherein said sealing bag is attached to said flange by a heat seal.

12. The sterile connector assembly of claim 6 wherein said connector is a hose barb connector.

* * * * *